United States Patent [19]

Green

[11] Patent Number: 4,608,868
[45] Date of Patent: Sep. 2, 1986

[54] ULTRASONIC REFLEX TRANSMISSION IMAGING METHOD AND APPARATUS

[75] Inventor: Philip S. Green, Menlo Park, Calif.
[73] Assignee: SRI International, Menlo Park, Calif.
[21] Appl. No.: 715,199
[22] Filed: Mar. 22, 1985
[51] Int. Cl.$^4$ .............................................. G01N 29/00
[52] U.S. Cl. .......................................... 73/606; 73/620
[58] Field of Search .................... 73/606, 607, 620; 128/660, 663; 367/7, 11

[56] References Cited

U.S. PATENT DOCUMENTS

| | | | |
|---|---|---|---|
| 3,918,025 | 11/1975 | Koshikawa et al. | 73/626 |
| 3,937,066 | 2/1976 | Green et al. | 73/607 |
| 4,016,750 | 4/1977 | Green | 73/629 |
| 4,163,394 | 8/1979 | Soldner | 73/626 |
| 4,305,296 | 12/1981 | Green et al. | 73/626 |
| 4,409,839 | 10/1983 | Taenzer | 73/625 |
| 4,413,520 | 11/1983 | Murakami et al. | 73/609 |
| 4,437,348 | 3/1984 | Sasaki | 73/625 |
| 4,457,175 | 7/1984 | Ramsey, Jr. et al. | 73/606 |
| 4,470,305 | 9/1984 | O'Donnell | 73/626 |
| 4,478,085 | 10/1984 | Sasaki | 73/625 |

OTHER PUBLICATIONS

H. Kanda et al., "Acoustic Microscope Observation of a Biological Specimen in a Total Reflector Backing Configuration" Ultrasonic Imaging 5, 161–194, Jun. 1983.

*Primary Examiner*—Stephen A. Kreitman
*Attorney, Agent, or Firm*—Victor R. Beckman

[57] ABSTRACT

An ultrasonic imaging system and method are disclosed which include a transducer (10) for pulse insonification (16) of an object (14) and for receiving echo signals from within the object. Echo signals are converted to electrical signals at the transducer (10) and the electrical signals are supplied to a signal processor (30) for processing the same. The signal processor (30) includes a detector (40) and integrator (42) for integrating the detector output.

Echo signals obtained from a range zone (Z) which is opposite the focal point (F) from the transducer (10) are integrated by integrator (42).

The amplitude of echo signals from range zone (Z) is strongly dependent upon attenuation at the focal point (F) whereby the integrator (42) output (60) also is dependent upon attenuation at the focal point (F). The integrator (42) output (60) is supplied to a display (48) for use in establishing one pixel thereof. A C-scan display is provided by scanning the focal point (F) in a focal plane (22) normal to the beam axis (20).

42 Claims, 14 Drawing Figures

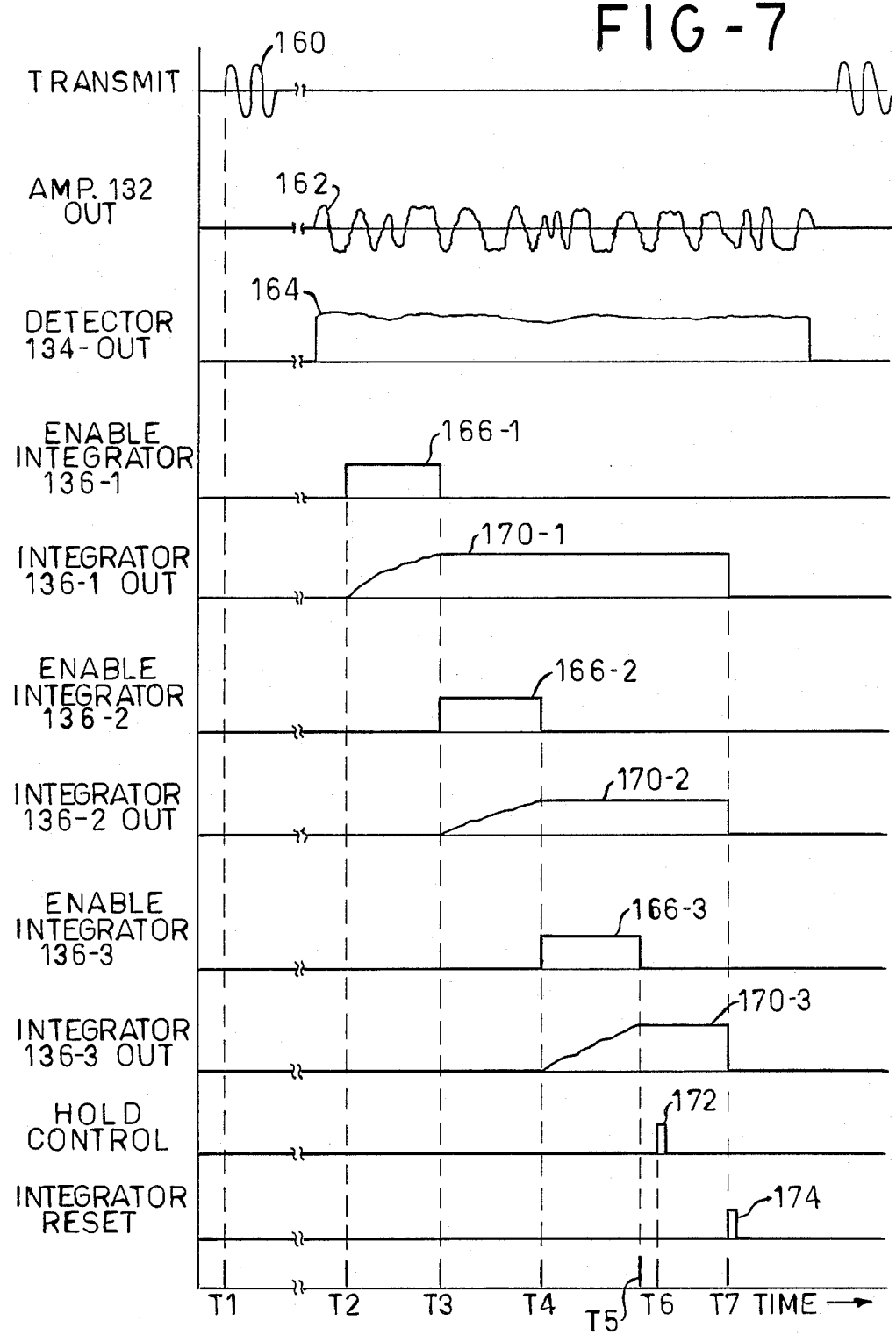

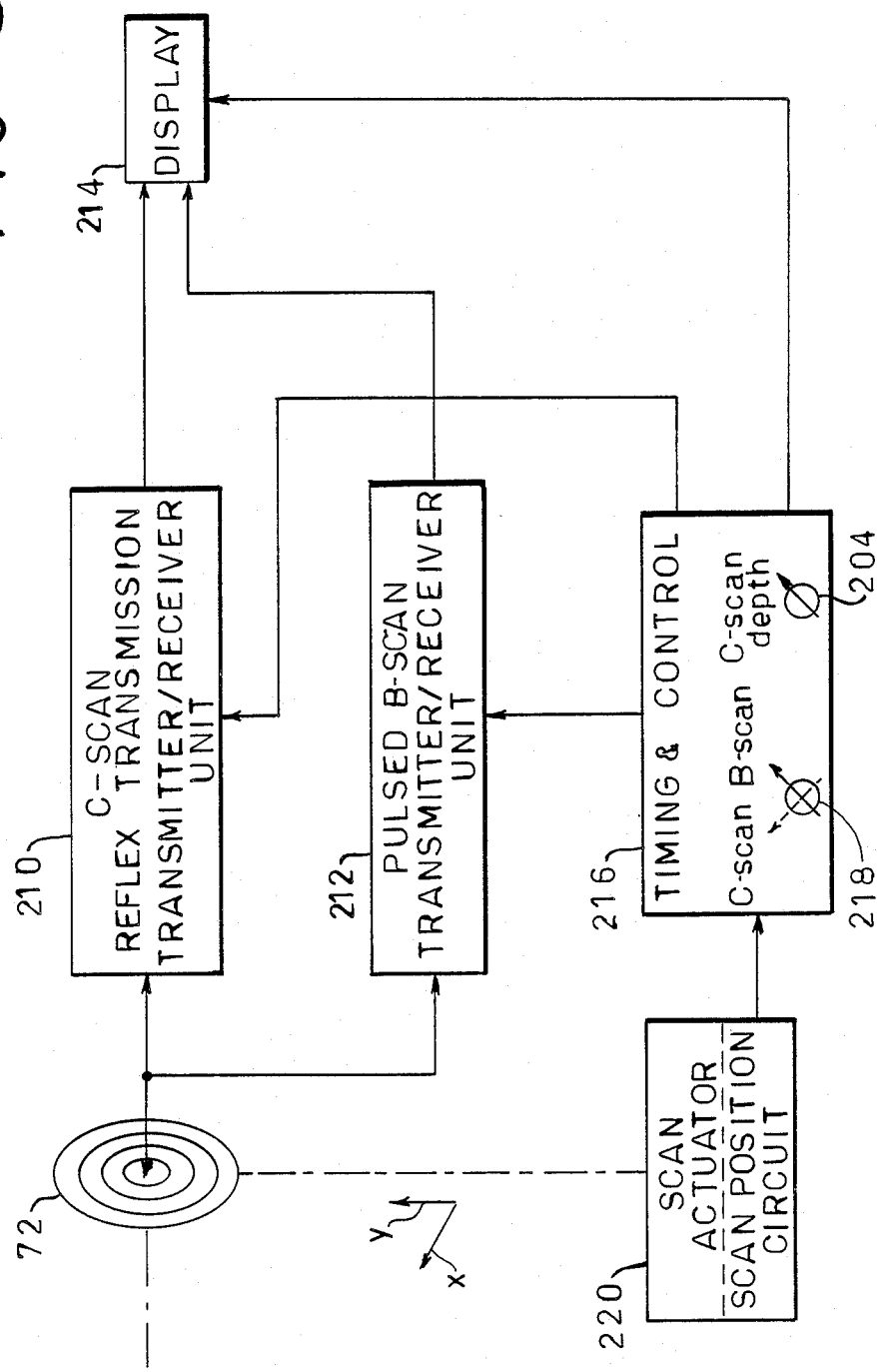

ULTRASONIC REFLEX TRANSMISSION IMAGING METHOD AND APPARATUS

FIELD OF THE INVENTION

This invention relates generally to an ultrasonic imaging method and apparatus.

BACKGROUND OF THE INVENTION

Ultrasonic imaging systems of the transmission type wherein a transmitting transducer and a receiving transducer are located at opposite sides of an object or specimen under examination are well known as shown, for example, in U.S. Pat. Nos. 3,937,066, Green et al and 4,457,175, Ramsey, Jr. et al. Generally C-scan images are provided by transmission type systems which lie in a plane normal to the transmitted waves. Echo type ultrasonic imaging systems also are well known as shown, for example, in U.S. Pat. Nos. 4,106,750, P. S. Green and 4,305,296, Green et al. Generally B-scan type images are produced wherein the image formed lies in a plane containing the propagated waves. Of course, C-scan images also may be obtained using echo techniques.

SUMMARY AND OBJECTS OF THE INVENTION

An object of this invention is the provision of an ultrasonic imaging system and method which combine features of echo and transmission type systems for improved imaging.

An object of this invention is the provision of a echo-transmission type ultrasonic imaging system and method in which a single transducer functions both to transmit and to receive ultrasonic waves.

An object of this invention is the provision of an ultrasonic imaging system of the above-mentioned type wherein reflected waves received from a range zone behind the focal point of the receiving transducer, which reflected waves insonify the object at the focal point, are processed so that the received signal represents information from the focal point and not specific information from the range zone from which the reflected signals are received.

An object of this invention is the provision of an ultrasonic imaging system and method of the above-mentioned type which may include a transducer which functions for both transmission and reception of ultrasonic waves without the need for separate transmitting and receiving transducers.

In accordance with the present invention a transmitter energizes a transducer for beaming ultrasonic energy into a section in an object to be examined. Ultrasonic energy waves reflected from within the object are received by the transducer where they are converted to electrical signals. Beam focusing means for focusing the transducer, and beam scanning means for scanning the section to be imaged are provided, either of which may be ultrasonically, mechanically or electronically implemented. The system includes signal processing means responsive to the electrical signal output from the transducer for processing signals received from a range zone located beyond the point at which the beam is focused. Signal processing includes detection of the signals from said range zone and time integration of the detected signals over the time period that said signals are received from the range zone. The integrated signal output, which represents information from the point at which the receiver transducer is focused, is supplied to display means and provides information for one pixel of the display.

The invention, together with other objects, features and advantages thereof will be more fully understood from a consideration of the following detailed description of certain embodiments thereof taken in connection with the accompanying drawings. It here will be understood that the drawings are for purposes of illustration only, the invention not being limited to the specific embodiments disclosed therein.

BRIEF DESCRIPTION OF THE DRAWINGS

In the drawings, wherein like reference characters refer to the same parts in the several views:

FIG. 7 is a timing diagram for use in explaining operation of the system shown in FIGS. 6A and 6B;

FIG. 8 is a block diagram showing a bi-modal imaging system for C-scan and B-scan imaging.

DETAILED DESCRIPTION OF THE INVENTION

Figure 1:
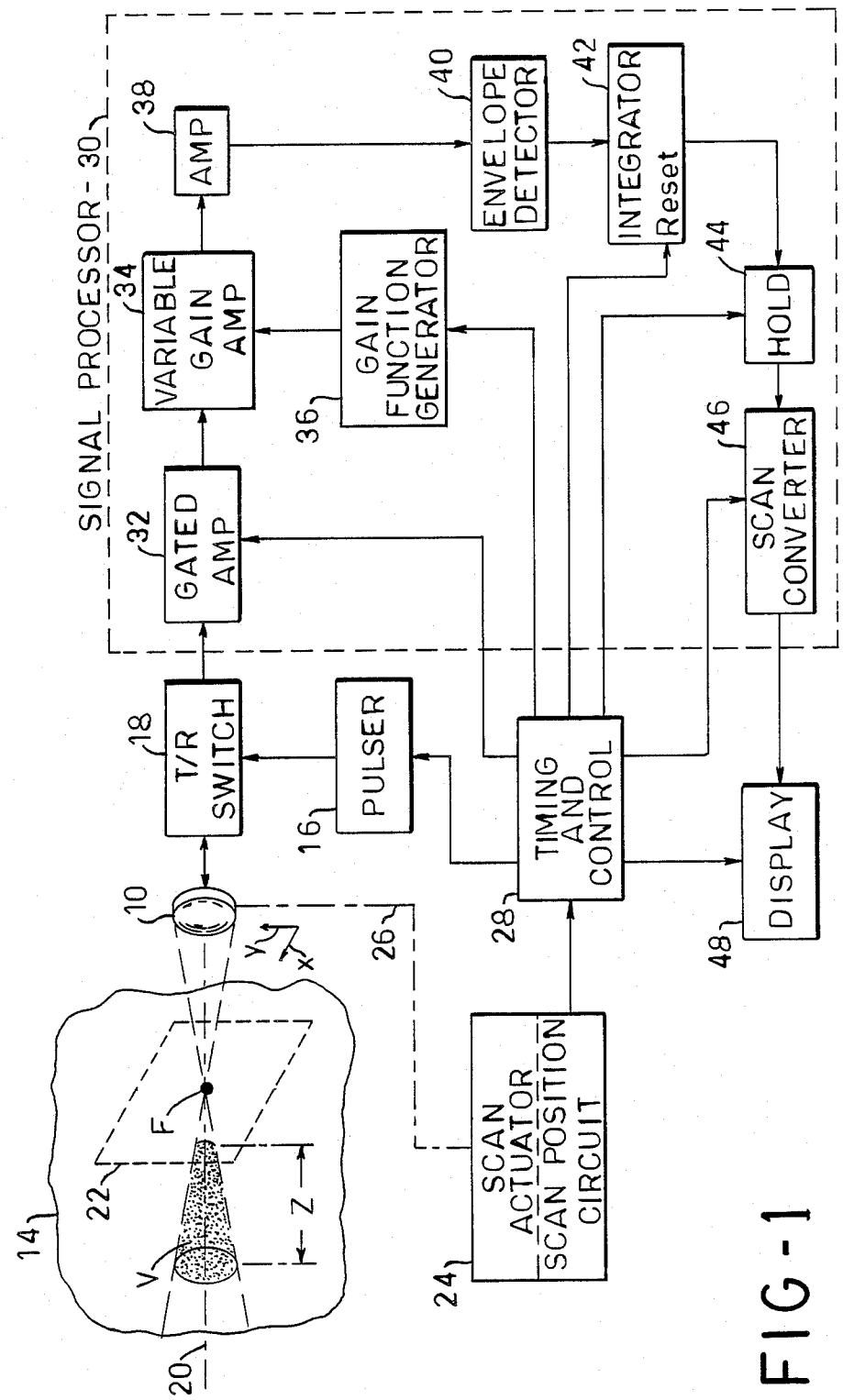
FIG. 1 is a block diagram showing an ultrasonic imaging system embodying the present invention.

Reference first is made to FIG. 1 wherein there is shown an ultrasonic imaging system comprising transducer 10 which, in the illustrated arrangement is used for transmitting and receiving ultrasonic pulse signals. For purposes of illustration, a curved focusing transducer is shown. Ultrasonic compressional waves generated by focusing transducer 10 are coupled through a suitable acoustic transmission medium such as water, not shown, to the subject 14 under investigation and are focused within the subject. Although the system is well adapted for imaging living organisms, it will be apparent that the invention is not limited to such particular application or use. In place of the focusing transducer, it will be apparent that other acoustical focusing means such as an acoustic lens, a curved acoustical mirror, or the like, may be employed. Also, electronic focusing may be employed in lieu of, or in addition to, acoustical focusing means. Also, as will become apparent hereinbelow, although focusing during both transmitting and receiving operations is preferred, focusing only during receiving operation or only during transmitting operation is required.

The transmitting portion of the system includes pulser 16 for recurrent generation of high frequency energy pulses which are supplied through transmit-receive switch 18 to transducer 10 for pulse generation of ultrasonic waves which are focused at focal point F within the subject 14. Typically, an operating frequency of from, say, 1 MHz to 10 MHz may be employed. The ultrasonic beam axis is identified by reference numeral 20 and, in the illustrated embodiment of the invention, a C-scan image of plane 22 normal to axis 20 is obtained by movement of the focal point F in the plane to scan the same. The transducer 10 and associated focusing lens 12 are scanned in the x and y directions shown in FIG. 1 by scan actuator 24 connected thereto through mechanical linkage 26. The scanning mechanism 24 includes a scan position information circuit having an output connected to timing and control unit 28 which, in turn, has outputs for synchronizing the transmitting, receiving, and display scanning operations.

Reflected ultrasonic signals from discontinuities, or scatterers, within the subject 14 received by transducer 10 are converted to electrical signals and supplied through transmit-receive switch 18 to a signal receiver, or processor, 30 which, for purposes of illustration, includes a gated amplifier 32. A preamplifier, not shown, may be included in the connection of the received signals to amplifier 32. A time gate signal is supplied to gated amplifier 32 from timing and control unit 28 for control of the receiving operation. In the illustrated embodiment, the receiver is gated on for processing of echo signals received from a volume V within a range zone Z located behind the focal plane 22 and focal point F located therein; that is from a zone located opposite the focal plane from the transducer. The range zone may be located adjacent focal point F and, if desired, the inner end of range zone may be located at focal point F. In the illustrated embodiment, only reflected signals received from within range zone Z are processed by signal processor 30. Obviously, echo signals received from different depths and/or range zones may be processed by other means, not shown.

Since return signals are received from a range of distances, Z, within the subject, received signals from gated amplifier 32 are amplified by variable gain amplifier 34, the gain of which is time varied in accordance with the output from a gain function generator 36. The timing of the operation of gain function generator 36 is under control of timing and control unit 28. The gain of amplifier 34 is increased in proportion to range so as to offset the loss of signal caused by acoustic absorption within the subject. If desired, a time gain function which approximates the condition wherein reflected waves passing through the focal point F from volume V are of equal amplitude may be employed.

From variable gain amplifier 34, received signals are shown coupled to amplifier 38 having a desired gain function. For example, amplifier 38 may comprise a linear amplifier or a non-linear amplifier.

The amplifier 38 output is detected as by envelope detector 40 comprising, for example, a full wave rectifier with low pass filter means and having as an output a signal which is proportional to the envelope of the high frequency signal output from amplifier 38. With the present invention, the detector output is supplied to an integrator 42 for time integration thereof during the period that signals are received from within range zone Z. After each integrating operation, the integrator output is supplied to a hold circuit 44 from whence it may be transferred to a scan converter 46 and thence to visual display means 48, such as a cathode ray tube, under control of timing and control unit 28. At the end of the receiving operation, after transfer of the integrator output to hold circuit 44, the integrator 42 is reset by application of a reset signal thereto over line 50 from timing and control unit 28 in preparation for the next transmit/receive cycle. In the FIG. 1 embodiment, information for display of a single pixel is obtained for each transmit/receive cycle.

Figure 2:
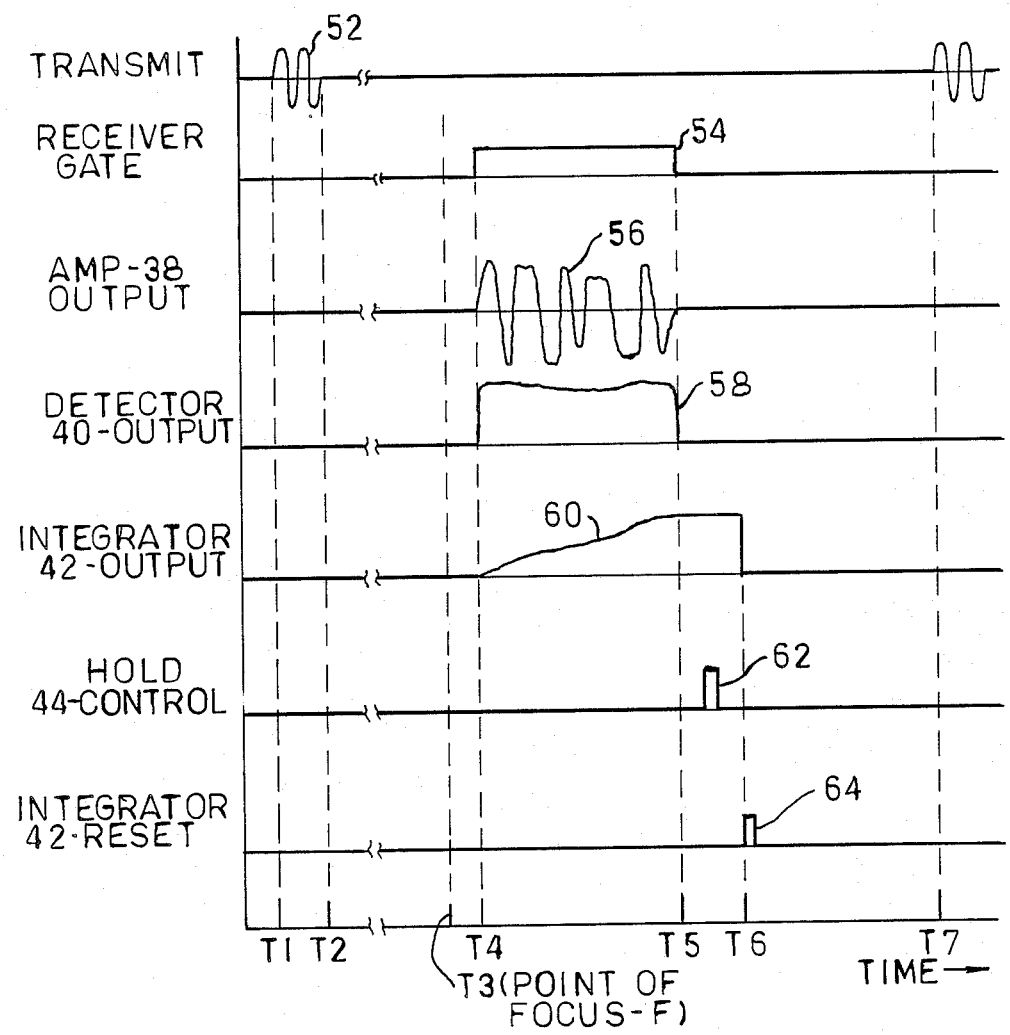
FIG. 2 is a timing diagram for use in explaining operation of the system shown in FIG. 1.

Although the operation of the ultrasonic imaging system of FIG. 1 is believed to be apparent from the above description, a brief description thereof with reference to the timing diagram of FIG. 2 now will be made. The focusing transducer 10 is moved across the object 14 in the x and y directions by scanning mechanism 24. A scan position signal is produced by the scan position circuit associated with the scanning mechanism and supplied to the timing and control unit 28 from which control signals for timing operation of the transmitter, receiver, and display means are obtained.

During the transmit period, between times T1 and T2, ultrasonic waves are generated by transducer 10 which is energized by the output from pulser 16. In FIG. 2, transmitter pulses are shown at 52. The ultrasonic wave pulse from focusing transducer 10 travels into the subject 14, and at time T3 echo signals reflected from focal point F are received by the transducer 10. After a time delay between times T2 and T4, the receiver is gated on by receiver gate signal 54 supplied to gated amplifier 32 from the timing and control unit for processing echo signals received from a range zone beyond the focal point F. The time gated received signal output from amplifier 38 is shown at 56 of FIG. 2. The received signal is detected by detector 40 having an output 58. The detected signal is integrated by integrator 42, the integrator output being shown at 60 in FIG. 2. After the receiver is gated off, at time T5, the integrator output is transferred to hold circuit 44 under control of hold control signal 62. Following such transfer, at time T6, the integrator 42 is reset by reset signal 64. The next transmit-receive cycle starts at time T7 with the transmission of another insonifying pulse 52.

From the above, it will be apparent that all of the transmitted energy, save that scattered and absorbed before the focal point F, is transmitted through the point of focus. It then spreads out and is scattered by inhomogeneities of the subject within the generally conical zone V behind the plane of focus 22. The distribution of scatterers behind the object provides an effective extended incoherent insonification source. As noted above, it will provide most effective insonification if the waves reflected through the focus from each lamina of range zone is of substantially the same amplitude, and this condition is approximated by time-gain correction of the receiver as noted above. However, if the signal to noise ratio at increased depths is too low, then a time-gain correction which provides for an improved signal to noise ratio at such depths may be employed.

Figure 3:
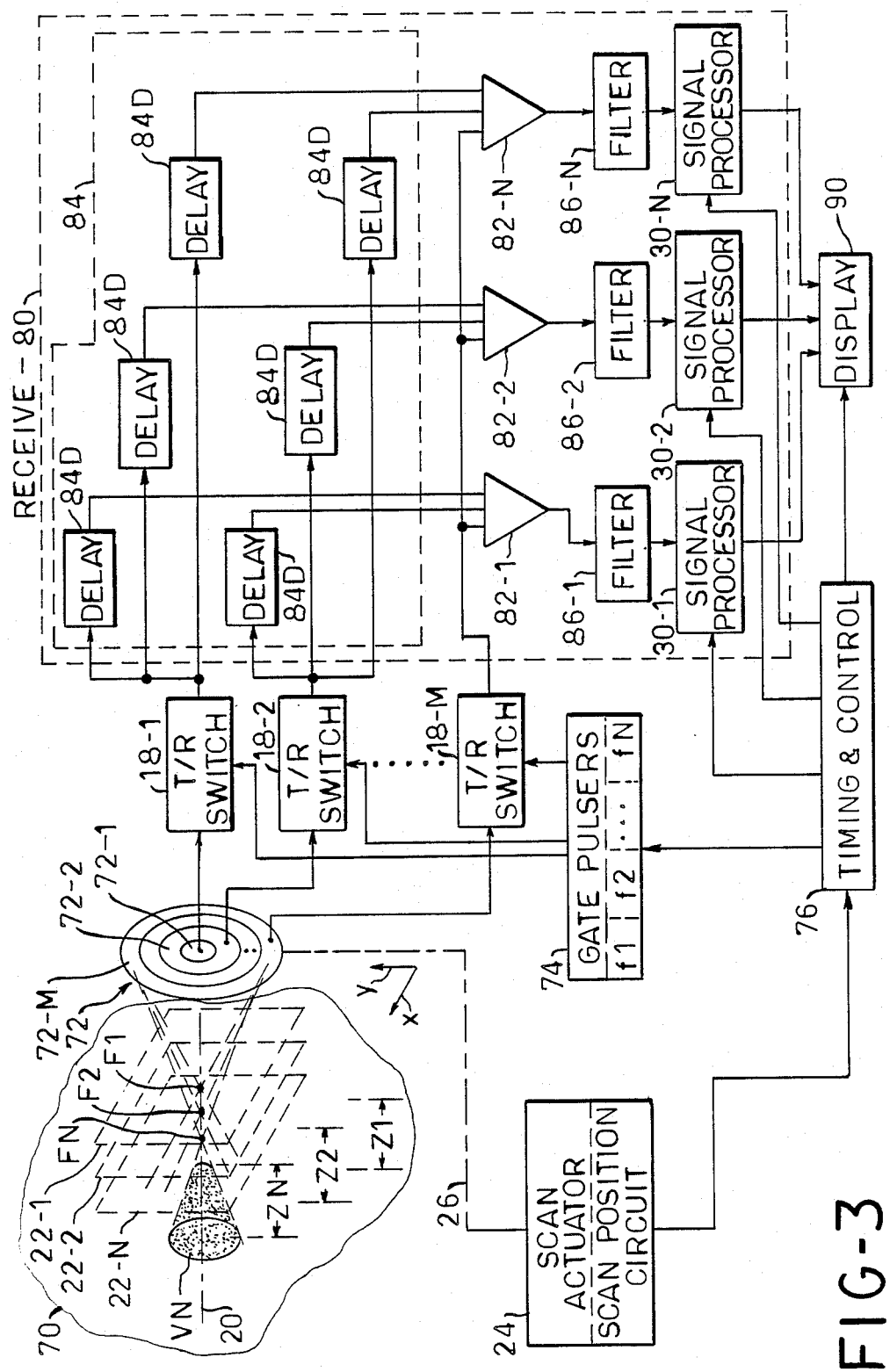
FIG. 3 is a block diagram showing a modified form of ultrasonic imaging system embodying this invention for use in three-dimensional imaging of an object.

Scattered waves are received by the transducer 10, but those passing through focus F have the most influence on the signal generated by the receiving transducer. Thus, the received waves pass through the focus twice, and their amplitude is strongly influenced by attenuation within it. It will be apparent, then, that a major advantage of the present invention is the ability to make transmission-type images by backscatter. Additionally, an improved signal-to-noise ratio is achieved as a result of the extended integration time, which also ensures the reduction of image speckle. Reference now is made to FIG. 3 of the drawings wherein a modified form of this invention for use in obtaining three dimensional images of a portion of the interior of a subject 70 is shown. In the illustrated arrangement information for imaging at a plurality of different planes 22-1, 22-2 ... 22-N within subject 70 is shown. An annular transducer array 72 is employed for pulse insonification and reception. For purposes of illustration only, a transducer which includes a central circular electrode 72-1 and concentrically disposed annular electrodes 72-2 through 72-M is shown.

The transmitting portion of the system includes a gated pulser unit 74 which includes a plurality of pulsers which operate at different center frequencies f1, f2, ... fN. On-off gating of pulsers included in unit 74 is under control of timing and control unit 76. Outputs from pulser unit 74 are connected to elements 72-1, through 72-M of annular array 72 through transmit/receive switches 18-1, through 18-M. Gated pulser unit 74 operates to supply elements of transducer 72 with first pulse signals of center frequency f1, the timing of which signals at the transducer elements providing for production of a focused beam having a focal point at F1 in focal plane 22-1. Next, second pulse signals of center frequency f2 are supplied to the transducer elements with proper timing for production of a beam which is focused in plane 22-2 at focal point F2. Finally, pulse signals of center frequency fN are supplied to the transducer elements with proper timing for pulse transmission of a beam which is focused at focal point FN in plane 22-N. A series of pulse insonifications at center frequencies f1, through fN take place in rapid succession before any echo signals are received from range zones beyond the points of focus and before signal processors for processing echo signals are gated on.

A signal receiver 80 for processing the different-frequency echo signals is shown comprising a plurality of summing amplifiers 82-1 through 82-N to which electrical signals produced by echo signals at transducer elements are supplied through the transmit/receive switches. Except for the outermost annular electrode 72-M, electrical signals from elements of the annular array are connected through time delay means 84 to the summing amplifiers for time delay focusing of the transducer. Here, a plurality of fixed signal delay elements 84D having appropriate time delays are shown for use in connecting electrodes of the transducer array to the summing amplifiers. As seen in FIG. 3 the outermost annular element 72-M is directly connected to the summing amplifiers without the need for delaying these signals.

Outputs from the summing amplifiers 82-1 through 82-N are connected to bandpass filters 86-1 through 86-N, respectively, for use in separating the different-frequency return signals. By using separate sets of delays, summers, and filters, receiver foci at a plurality of depths at which the transmitted bursts are focused are provided. The frequency-separated electrical signals are processed at signal processors 30-1 through 30-N which may be of the same type as signal processor 30 shown in FIG. 1 and described above. The signal processors are gated on under control of timing and control unit 76 for processing signals from range zones behind the associated focal points. In FIG. 3, the range zone ZN and associated volume VN from which echo signals are received for obtaining information concerning focal point FN are shown, together with range zones Z1 and Z2. The image planes are scanned by movement of the annular array 72 along the x and y axes under control of scan actuator and scan position circuit 24. Outputs from signal processors 30-1 through 30-N are shown supplied to visual display means 90 for selective or simultaneous display of the images obtained from the different image planes. For simultaneous display, the signal processor outputs may be displayed in separate color for distinguishing therebetween at the display 90. Alternatively, the outputs may be combined to form stereoptic pairs, or otherwise combined, or displayed separately.

Figure 4:
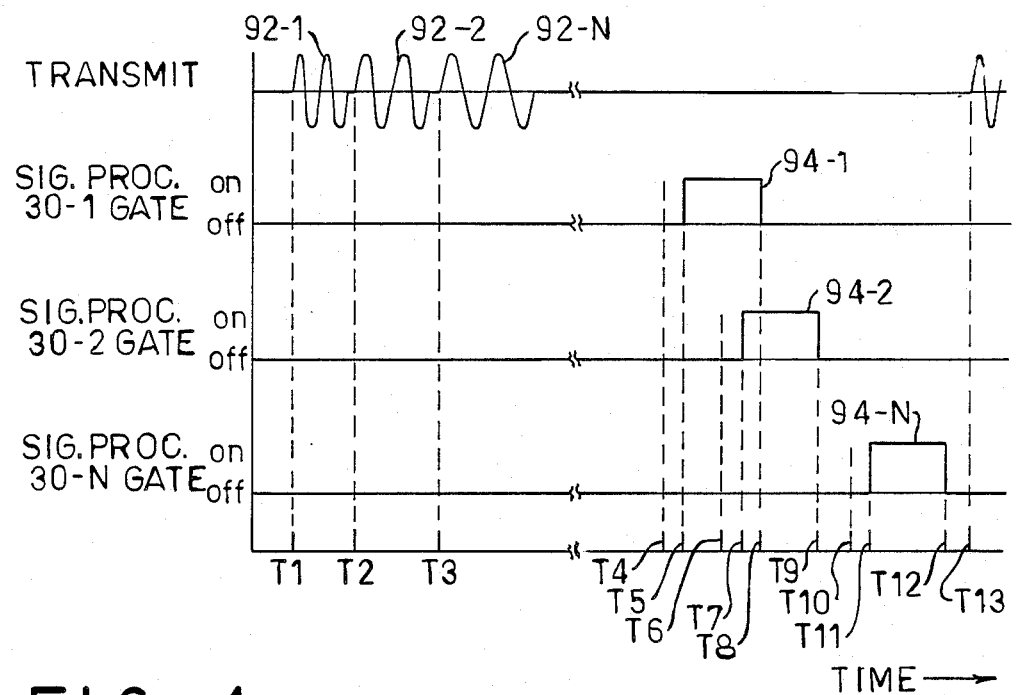
FIG. 4 is a timing diagram for use in explaining operation of the system shown in FIG. 3.

A brief description of the operation of the system shown in FIG. 3 now will be provided with reference to the timing diagram of FIG. 4. Pulses 92-1, 92-2 and 92-N which are focused at focal points F1, F2 and FN, respectively, are transmitted in rapid succession at times T1, T2 and T3 by the transducer array 72 under control of gated pulser unit 74. It here will be noted that it is not necessary to use short pulses as B-scan requires. Longer pulses permit the use of higher average transmit power and better rejection of receiver noise. However, the use of longer pulses leads to instantaneous reception of signals from over wider lamina within the range zone which, in turn, results in a greater statistical fluctuation of reflected signal power. The pulse length simply may be selected so as to maximize the signal to noise ratio in a particular object under investigation. Moderately narrowband transmitted bursts, each focused at a different depth and with center frequencies approximately inversely proportional to the focal distance may be employed. At times T4, T6 and T10 waves reflected from the respective focal points F1, F2 and FN by pulses 92-1, 92-2 and 92-N are received. Subsequently signal processors 30-1, 30-2 and 30-N are gated on at times T5, T7 and T11, and are gated off at times T8, T9 and T12, respectively, by gate signals 94-1, 94-2 and 94-N. The above-described transmit/receive cycle is repeated starting at time T13. Range-gated received signals are detected and integrated at the signal processors in the manner described above with reference to FIGS. 1 and 2, in preparation for display at display unit 90. The above-described system is well adapted for use in combination with Doppler blood flow measurement means with the ability to display a three-dimensional reflex transmission image and superimposed images of blood flowing through vessels substantially at the image planes.

Figure 5:
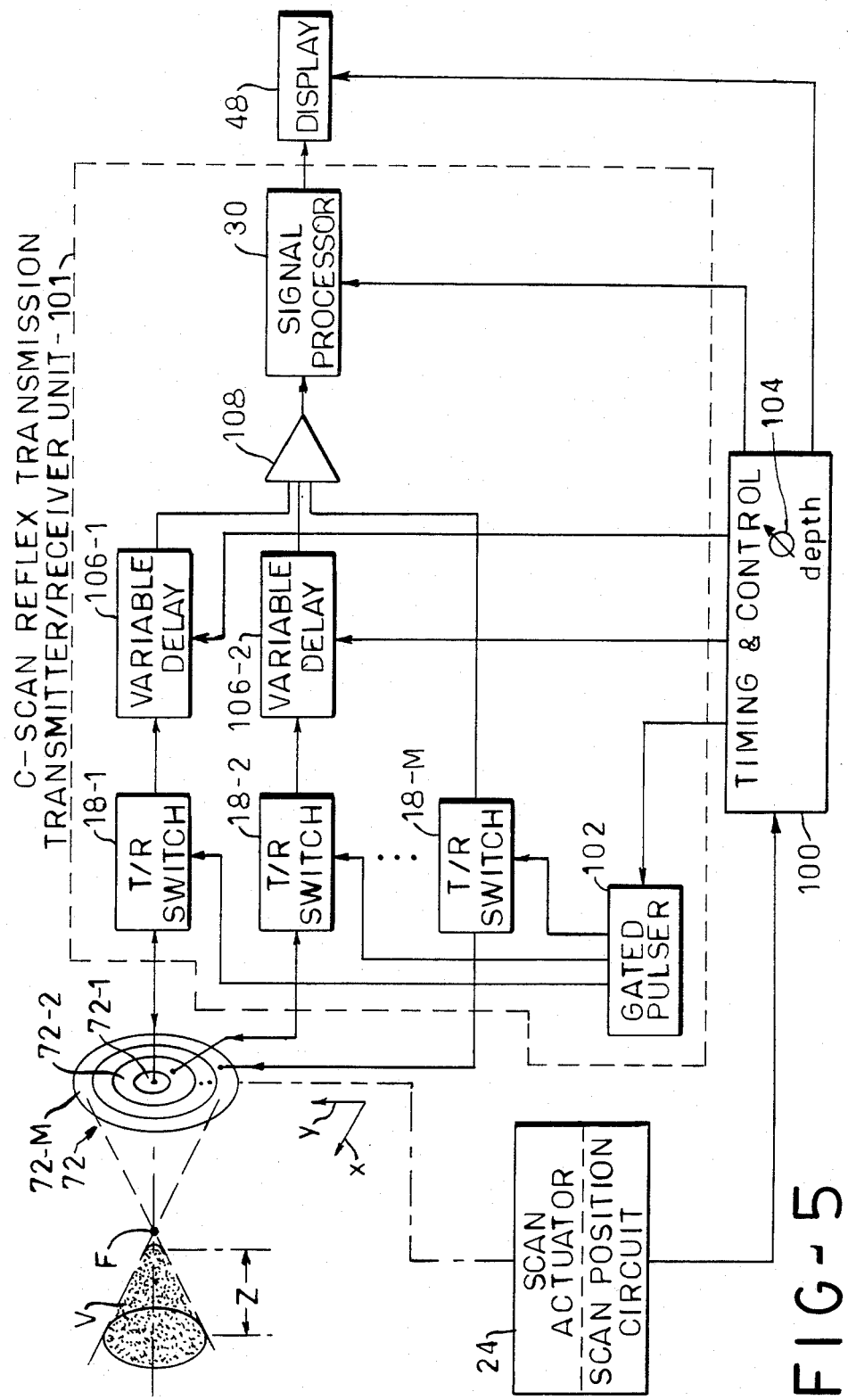
FIG. 5 is a block diagram showing another modified from an ultrasonic imaging system embodying this invention for use in C-scan imaging of the object at selected planes, FIGS. 6A and 6B together show a block diagram of another modified form of this invention which also is used for three-dimensional imaging of an object.

Reference now is made to FIG. 5 of the drawings wherein a modified form of this invention is shown which is adapted to obtain C-scan images at selected focal planes. The system illustrated in FIG. 5 includes an annular transducer array 72 such as employed in the arrangement of FIG. 3, which includes array elements 72-1 through 72-M. A scan actuator and scan position circuit 24 mechanically moves the transducer in two dimensions along the x and y axes, and supplies position signals to timing and control unit 100. The transmitter/receiver unit 101 includes a gated pulser 102 which is connected to the array elements through transmit/receive switches 18-1 through 18-M. Pulser 102 operates at a single center frequency, and timing of the gating of the output therefrom to the elements of the transducer array provides for focusing of the transmitted ultrasonic pulse at a selected depth under control of depth control 104 at timing and control unit 100.

Electrical signals produced by echo waves at the transducer elements are supplied to summing amplifier 108. Variable delay means are included in the connection of all but the outer annular element 72-M of the transducer array to the summing amplifier for focusing of the received signal at the same focal point at which the transmitted pulse is focused under control of depth control 104. In FIG. 5 two of the variable delay means 106-1 and 106-2 for connection of annular transducer elements 72-1 and 72-2, respectively, to the summing amplifier are shown. Signal processor 30 of the same type shown in FIG. 1 and described above processes the signal to provide a C-scan image at display unit 48. On-off gating of the gating amplifier included in the signal processor also is under control of depth control 104 for controlling the range zone from which echo signals are processed in association with the transmit and receive focal points established by the setting of depth control 104.

Figure 6A:
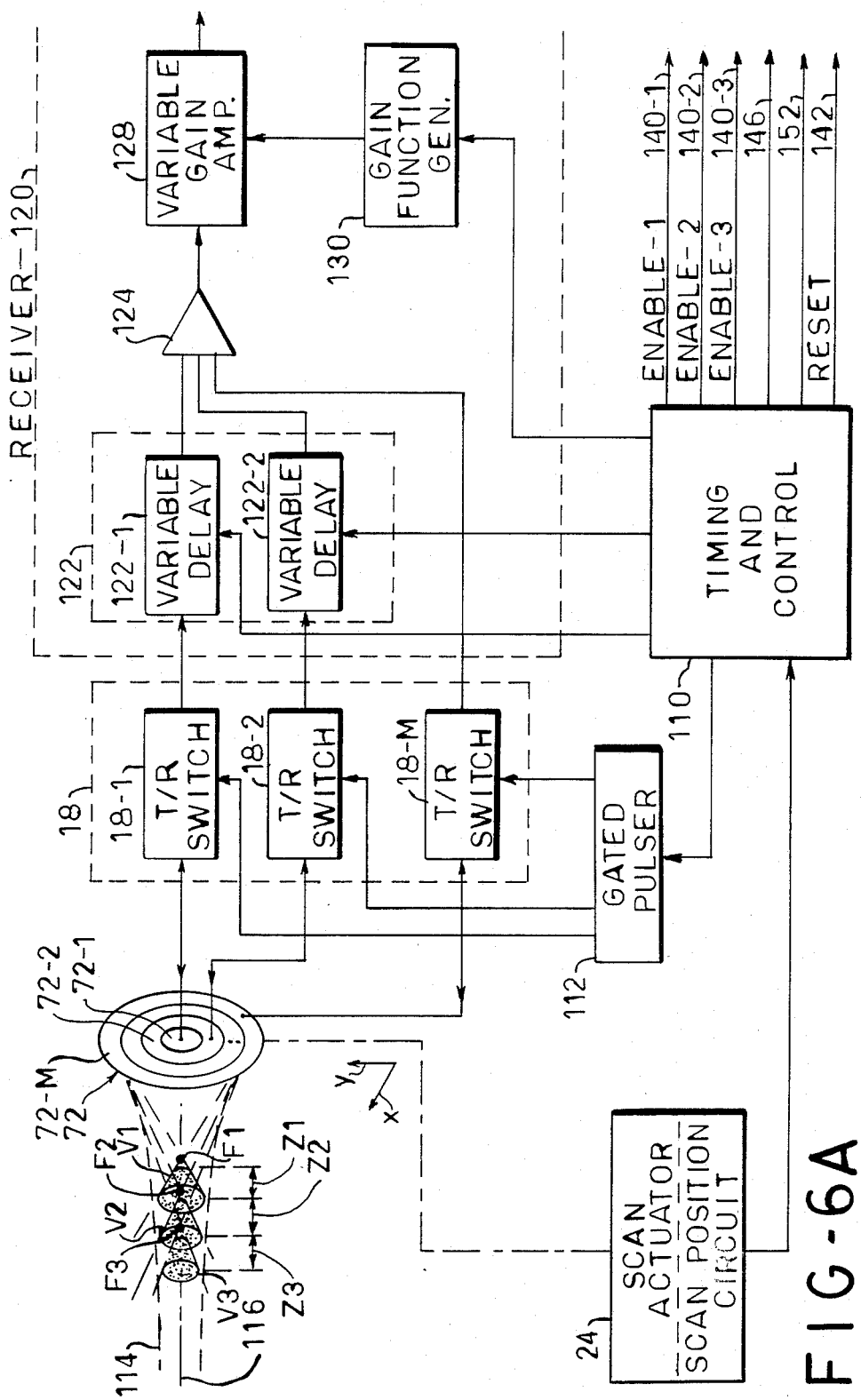
Figure 6B:
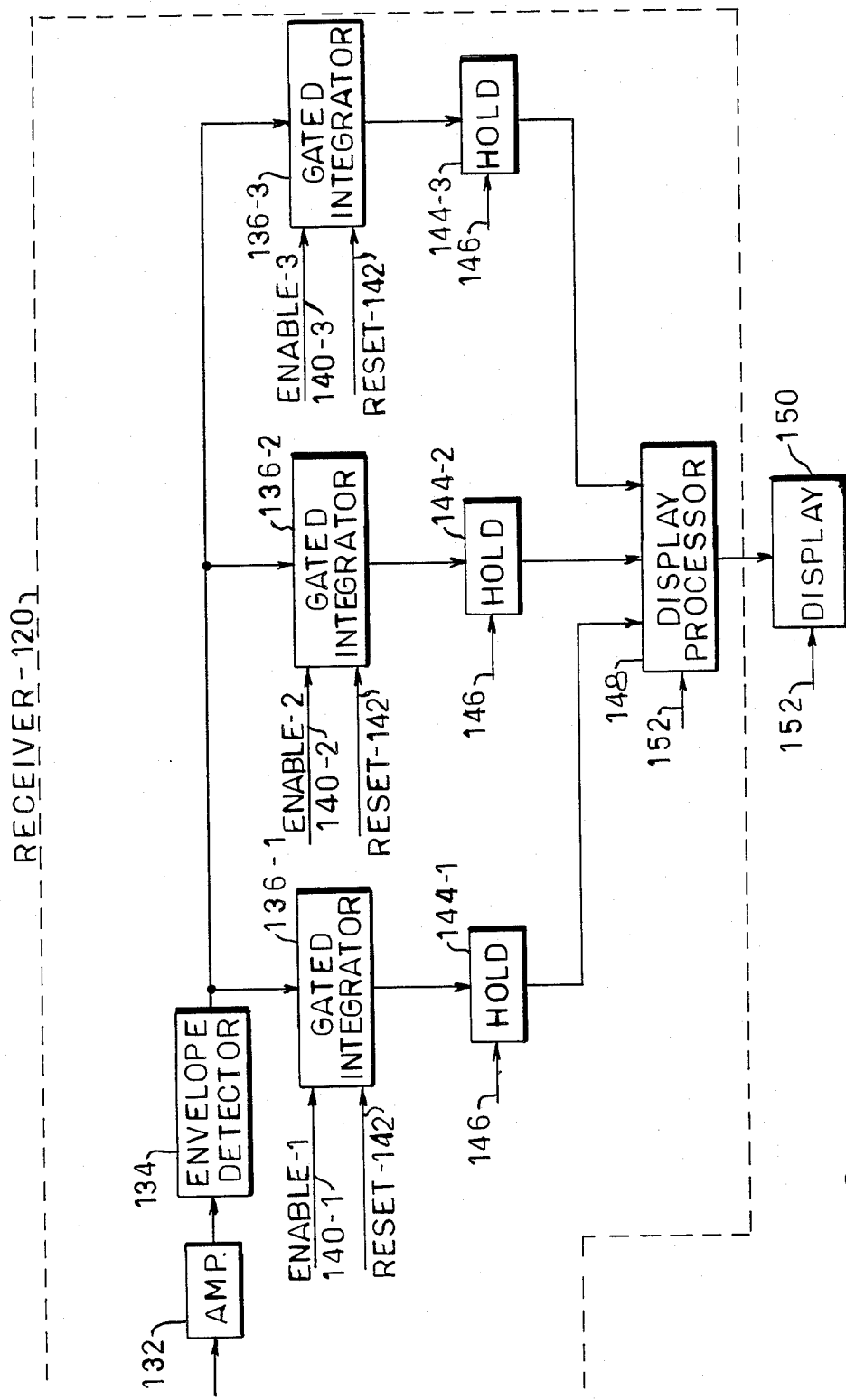

Another modified form of this invention for use in obtaining three dimensional images is shown in FIGS. 6A and 6B to which figures reference now is made. In this modification a single frequency signal is transmitted rather than a series of pulses having different center frequencies such as employed in the FIG. 3 embodiment. The illustrated imaging system includes an annular transducer array 72 which may be of the same type shown in FIGS. 3 and 5, which array includes transducer elements 72-1 through 72-M. A scan actuator and scan position circuit 24 mechanically moves the transducer along the x and y axes, and supplies position signals to timing and control unit 110.

The transmitting portion of the system includes a gated pulser 112 which is connected to the transducer array elements through transmit/receive switches 18-1 through 18-M. Pulser 112 operates at a single center frequency, and timing of the gating of the output therefrom to individual transducer elements provides for mild focusing of the transmitted pulse. The mildly focused transmitted beam is identified by reference numeral 114, and the transducer axis is identified by reference numeral 116. During reception, the transducer is successively focused at focal points F1, F2, and F3 for obtaining information relative to three different parallel planes in which the focal points are located, which planes extend substantially normal to the beam axis 116. For clarity of illustration the image planes are not shown in FIG. 6A. However, they may be located similarly to planes 22-1, 22-2 and 22-N shown in FIG. 3 described above.

The signal receiver 120 for processing electrical signals produced by echo waves at the transducer elements and connected thereto through the transmit/receive switches 18-1 through 18-M includes a summing amplifier 124. Received signals from all but the outer transducer element 72-M are connected to the summing amplifier 124 through variable delay means 122, two of which variable delay elements 122-1 and 122-2 are shown in FIG. 6A for connecting transducer elements 72-1 and 72-2 to the summing amplifier. The variable delay means are controlled by outputs from timing and control means 110 whereby during reception of echo signals by transducer 72 the transducer is successively focused at focal points F1, F2 and F3.

The summing amplifier 124 output is supplied to variable gain amplifier 128, the gain of which is time varied in accordance with the output from gain function generator 130. Timing and control unit 110 controls operation of gain function generator 130 so as to increase the gain of amplifier 128 in proportion to range so as to offset signal loss within the subject with depth. Amplified signals from variable gain amplifier 128 are further amplified at amplifier 132 (FIG. 6B) and the output from amplifier 132 is detected as by use of envelope detector 134.

This embodiment of the invention includes a plurality of gated integrators 136-1, 136-2 and 136-3 to which the detected signal from detector 134 is supplied. The integrators 136-1 through 136-3 are successively enabled, i.e. gated on, by enable signals supplied thereto from timing and control unit 110 over lines 140-1 through 140-3, respectively. The gated integrators are reset by a reset signal supplied thereat from timing and control unit 110 over line 142. The gated integrators 136-1 etc. and variable delays 122-1 etc. are controlled by timing and control unit 110 in a manner such that during the receiving portion of the transmit-receive cycle transducer 72 is successively focused at focal points F1, F2 and F3 while integrators 136-1, 136-2 and 136-3 are sequentially enabled for integrating detected signals obtained from range zones Z1, Z2 and Z3, respectively, located beyond the associated focal points.

Outputs from integrators 136-1, 136-2 and 136-3 are transferred to hold circuits 144-1, 144-2 and 144-3, respectively, which hold circuits are controlled by timing and control unit 110 connected thereto over line 146. Signals from the hold circuits, which are related to acoustic absorption at the focal points, are supplied to a display processor 148 in preparation for display at visual display means 150. Timing signals for proper timing of the display and display processor are supplied thereto from timing and control unit 110 over line 152.

A brief description of the operation of the imaging system shown in FIGS. 6A and 6B now will be made with reference to the timing diagram of FIG. 7. As the electronically focused transducer 72 is moved across the object under investigation in the x and y directions by scanning mechanism 24, a scan position signal is produced and supplied to timing and control unit 110 for use in system timing. At time T1 the transducer 72 is energized by the output from gated pulser 112 for generation of a transmitter pulse 160 which is coupled to the object, not shown, for pulse insonification thereof. The transmitted pulse beam is mildly focused as indicated by beam 114 in FIG. 6A.

The output from amplifier 132 in the receiver 120 is identified by reference numeral 162 in FIG. 7, and the detector 134 output is identified by reference numeral 164. Enable signals 166-1, 166-2 and 166-3 sequentially enable gated integrators 136-1, 136-2 and 136-3, respectively, whereby the detector 134 output 164 is integrated by integrator 136-1 between times T2 and T3, by integrator 136-2 between times T3 and T4, and by integrator 136-3 between times T4 and T5 while signals are received from range zones Z1, Z2 and Z3, respectively. Outputs from integrators 136-1, 136-2 and 136-3 are identified by reference characters 170-1, 170-2 and 170-3, respectively. While integrators 136-1, 136-2 and 136-3 are enabled, variable delay means 122 is controlled so as to focus transducer 72 at focal points F1, F2 and F3, respectively. Thus, between times T2 and T3, transducer 72 is focused at focal point F1, between times T3 and T4 it is focused at focal point F2, and between times T4 and T5 it is focused at focal point F3, whereby the zones from which received signals are processed are beyond the associated focal points. At time T6 the integrator outputs are transferred to hold circuits 144-1 through 144-3 by hold control signal 172. The hold circuits outputs are supplied to the display processor 148 for processing in preparation for display at display unit 150. At time T7 the integrators are reset by reset signal 174 in preparation for the next transmit-receive cycle.

It here will be apparent that operation of the FIGS. 6A and 6B arrangement is not limited to receiving signals from adjacent range zones Z1 through Z3. Instead, the range zones from which signals are processed may be spaced from each other. With suitable spacing between range zones, the system may include a single gated integrator for integrating signals obtained from the spaced range zone. With such an arrangement, the integrator output is transferred therefrom, and the integrator reset, after the receipt of signals from each range zone.

A bi-modal instrument which combines the variable-depth reflex transmission C-scan imaging system shown in FIG. 5 with a conventional B-scan system is illustrated in FIG. 8, to which Figure reference now is made. There, a C-scan reflex transmission transmitter/receiver unit 210 and annular transducer array 72 are shown which may be of the same type shown in FIG. 5 and described above. A conventional pulsed B-scan transmitter/receiver unit 212 also is connected to the annular transducer array 72. C-scan and B-scan images from units 210 and 212 are displayed at display unit 214. A timing and control unit 216 provides timing and control signals to the C-scan, B-scan and display units, and includes switch control 218 for selecting between C-scan and B-scan operation. For C-scan operation, scan actuator 220 connected to transducer 72 moves the transducer along the x and y axes. When switched to B-scan operation, scan actuator 220 functions to move transducer 72 back and forth along a single axis, say the x axis. With this bi-modal instrument, the depth of an item of interest within the subject may be ascertained using the B-scan mode, and the C-scan depth control 204 then may be set for operation at such depth for C-scan imaging thereat.

Figure 9:
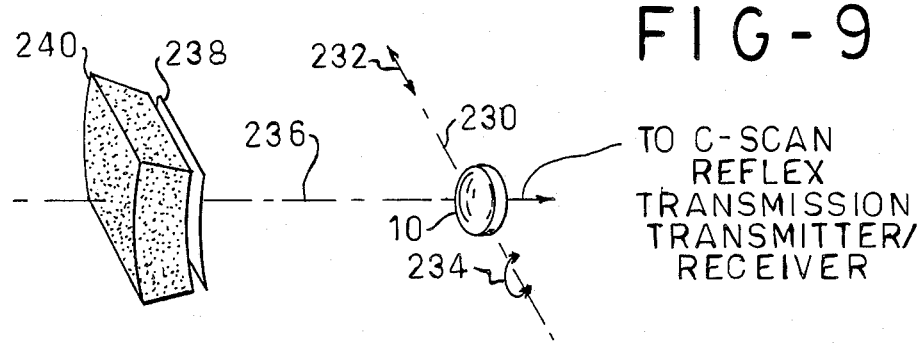
FIGS. 9, 10, 11 and 12 illustrate different transducer scanning means for use in reflex-transmission ultrasonic imaging systems of this invention.

The novel reflex-transmission method of this invention may employ a variety of scanning methods, and different types of ultrasonic transducers. For example, sector scanning may be employed in place of, or in combination with, linear scanning. Also, either mechanical or electronic scanning may be employed, or a combination thereof. Referring to FIG. 9, a transducer 10 is shown which may be of the type included in the imaging system shown in FIG. 1, except that the transducer is moved with a compound motion which includes rectilinear movement back and forth along axis 230 as indicated by arrow 232, and rocking motion about axis 230 in the direction of arrow 234. The beam axis is identified by reference numeral 236, and the transducer is focused at a point on surface 238. Echo signals received from zone 240 opposite surface 238 from the transducer are processed by the receiver of an associated C-scan reflex-transmission transmitter-receiver unit of the general type shown in FIG. 1 for imaging of the surface 238.

Figure 10:
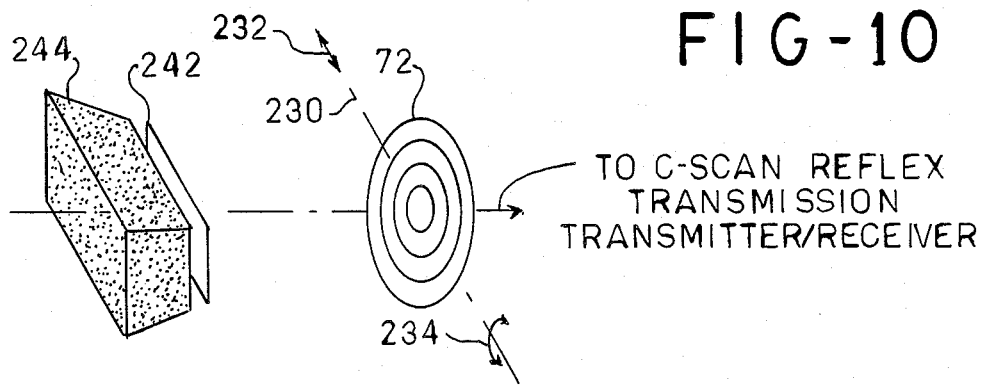

In FIG. 10, to which reference is made, an annular transducer array 72 is shown which is provided with the same rectilinear and scanning motions as transducer 10 shown in FIG. 9 and described above. A reflex-transmission transmitter-receiver unit of the general type shown in FIG. 5 may be used for energizing the transducer and processing echo signals. The transducer 72 is focused at plane 242, and echo signals from zone 244 opposite the surface 242 from the transducer are processed by the receiver. Timing of gated pulsers in the transmitter is adjusted for focusing at the plane 242 during pulse transmission, and variable delay means in the receiver are controlled for focusing at said plane during receiving operation.

Figure 11:
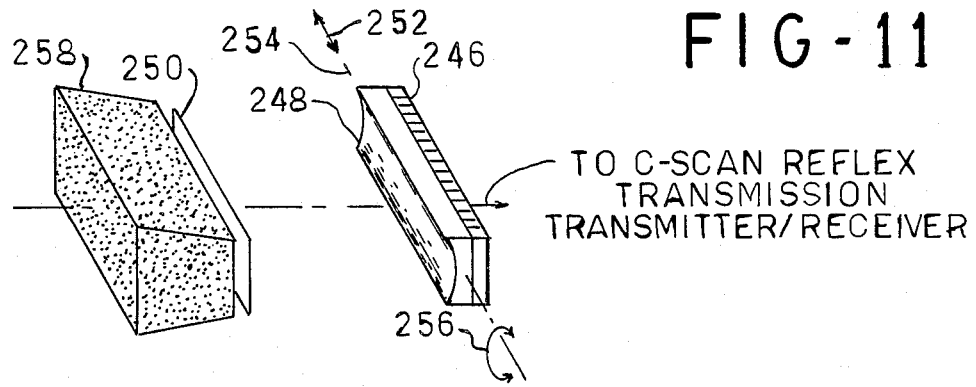

In FIG. 11, a linear transducer array 246 with a cylindrical focusing lens 248 is shown for use in conjunction with a reflex-transmission transmitter-receiver. Elements of the transducer array are operated in groups for focusing at plane 250 and for beam scanning in the direction of arrow 252. The transducer is rocked about axis 254 in the direction of arrow 256. A reflex-transmission transmitter-receiver unit of the general type shown in FIG. 5 and described above may be used in the FIG. 11 arrangement. Groups of transducer elements are energized by gated pulsers included in the transmitter to provide for beam scanning and focusing, in a manner well understood in this art. Signals reflected from zone 258 opposite plane 250 from the transducer are processed by the receiver to obtain an image of plane 250.

Figure 12:
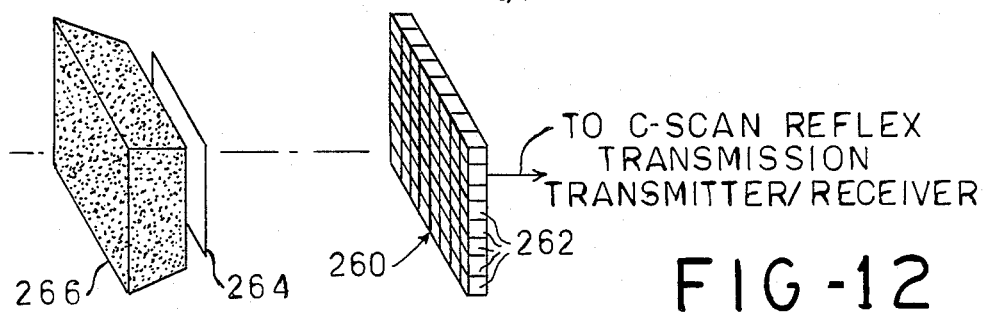

A reflex transmission system employing a two dimensional transducer array is shown in FIg. 12 of the drawings, to which figure reference now is made. The two dimensional transducer 260 included therein includes columns and rows of transducer elements 262, and for purposes of illustration only, an array having an equal number of column and rows of transducer elements is shown. With this array, both focusing and scanning of the array is effected electronically by energizing groups of transducer elements with properly phased signals, and by employing groups of transducer elements and associated delay means when receiving the echo signals. The associated C-scan transmission reflex transmitter-receiver to which the transducer array is connected includes electronic circuitry required for such focusing and scanning operations in a manner well known in the prior art. The transducer array is focused at plane 264, and signals reflected from zone 266 oppositie plane 264 from the transducer array are processed by the receiver to provide an image of plane 264 in a manner described above.

Figure 13:
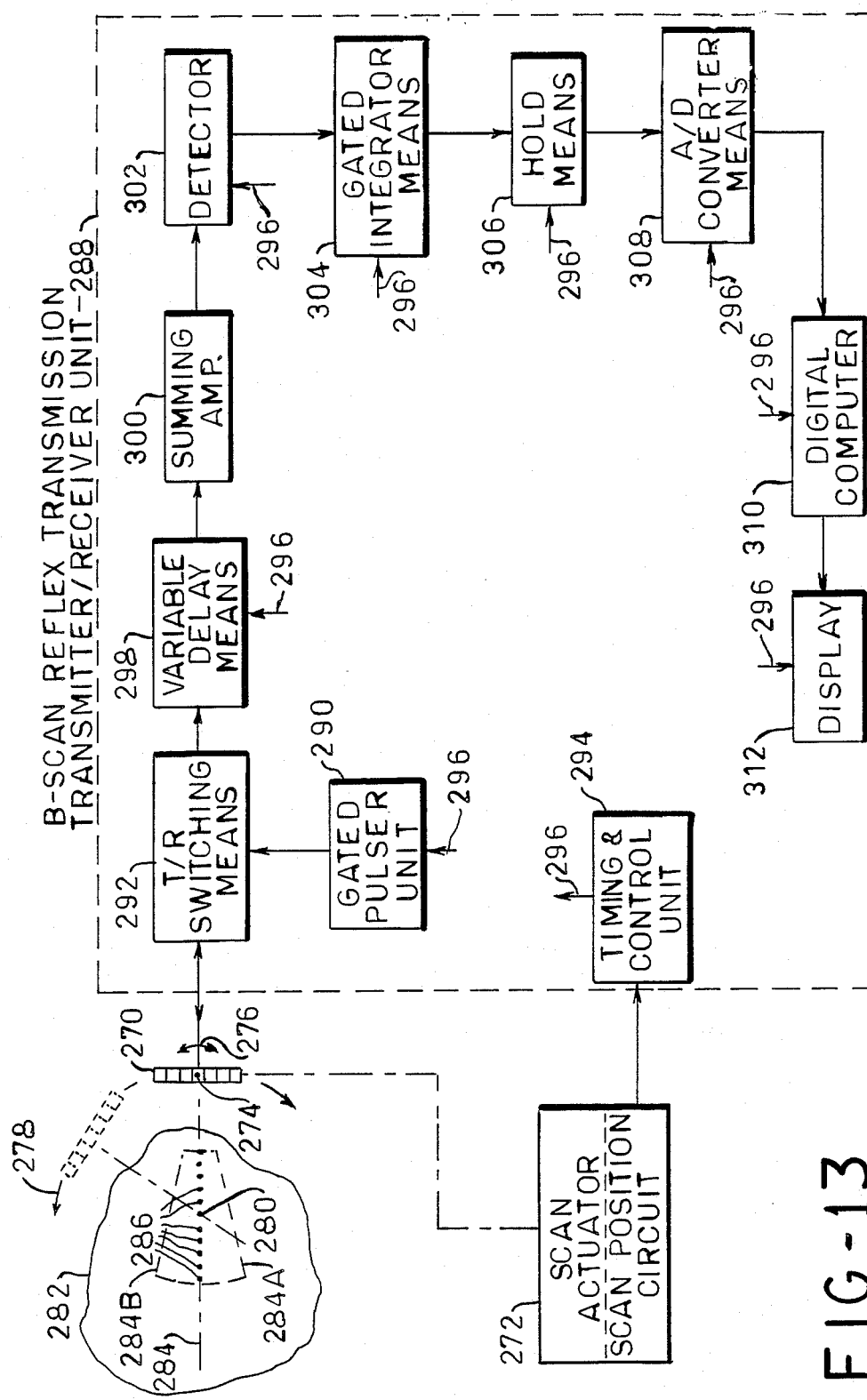
FIG. 13 is a block diagram showing a B-scan reflex-transmission ultrasonic imaging system which embodies this invention.

Although C-scan imaging systems are disclosed above, it will be apparent that the novel reflex-transmission method of this invention is not limited to C-scan imaging. For purposes of illustration a B-scan imaging system using the reflex-transmission technique is shown in FIG. 13, to which figure reference now is made. The system includes an annular transducer array 270 comprising a plurality of annular transducer elements surrounding a central circular transducer element. A scan actuator and scan position circuit 272 imparts a compound scanning motion to the transducer by rocking the same about pivot axis 274 as indicated by double-headed arrow 276 and by moving it in a circle, or sector of a circle 278, about an axis 280 located in a subject 282 under examination. As seen in the full line position of the transducer array, the transducer axis 284 is sector scanned between scan end positions 284A and 284B. Information concerning the acoustic absorption of a plurality of points 286 along the acoustic axis 284 at which the transducer is focused is obtained from signals reflected from zones which are opposite the focal points from the transducer, in the manner described above.

The transducer is connected to a B-scan reflex-transmission transmitter-receiver unit 288 which includes a gated pulser unit 290 connected to the transducer through transmit-receive switch means 292. Timing signals for the gated pulser means, and other elements of the system, are supplied by timing and control unit 294 over line 296. The gated pulser unit may be operated to provide either a sharply focused pulse, as in the FIG. 5 system, or a mildly focused pulse, as in the FIGS. 6A and 6B system.

Assume, for purposes of description, that the transmitted beam is mildly focused and that during receiver opertion, the transducer is sequentially focused at focal points 286 for obtaining information concerning acoustic absorption at said points. Focusing of the transducer at the different focal points during echo signals reception is under control of variable delay means 298. Outputs from the variable deleay means are supplied to summing amplifier 300 for combining outputs from individual transducer elements of the transducer array.

The summing amplifier output is detected at detector 302, the output from which is supplied to gated integrator means 304 comprising a plurality of gated integrators for integrating echo signals received from a succession of range zones located opposite the focal points from the transducer array. The integrator outputs are supplied to individual hold circuits included in hold means 306. The outputs from the individual hold circuits are converted to digital form at analog to digital converter means 308. The digitized signals are supplied to a digital computer 310 for storage and processing with signals obtained from along other lines as the transducer axis is scanned. Processed signals from the computer 310 are supplied to display means 312 for B-scan display thereof. It will be apparent that although focal points 286 are shown, focusing as a practical matter takes place over a range of distances often identified as the focal zone. Without compound scanning the B-scan image would be of relative poor quality. However, when used with a compound scanning motion such as shown in FIG. 13, a B-scan, tomographic view, with high resolution is provided.

The invention having been described in detail in accordance with requirements of the patent statutes, other changes and modifications will suggest themselves to those skilled in this art. Other transducer configurations such as two dimensional arrays of transducer elements may be employed, so long as focusing is provided. As noted above either mechanical or electronic focusing and/or scanning may be employed, or a combination thereof. In addition, the reflex transmission imaging method disclosed herein may be employed in lens/conjugate-plane imaging systems such as that disclosed in U.S. Pat. No. 3,937,066, P. S. Green et al, issued Feb. 10, 1976, by placing the sound source behind the lens and incorporating the above-described reflex transmission imaging process.

For operation with many subjects, reasonably uniform reflex insonification can be achieved, particularly if the f/number of the focusing transducer means is low whereby the cone of scatterers behind the focal plane is large. Nonuniformity of scatter density behind tthe focal point could contribute to low-spatial-frequency variations in the field insonifying each focal plane. These variations, as well as the effects of attenuation from out-of-the focal-plane regions if not adequately removed by the integration may be further reduced by various methods of post processing of received signals. Obviously, digital signal processing methods rather than the analog ones shown and described herein, may be employed. In addition, receiver operations may be performed by software in a suitably programmed computer, or computers. Also, separate transmitting and receiving transducers which are closely located may be employed, if desired. Obviously, gating of the receiver, or signal processor, at points other than at a gated amplifier at the receiver input or by gated integrators is contemplated. Furthermore, it will be apparent that a chirped signal, or otherwise coded signal source, may be employed to generate a chirped or otherwise coded ultrasonic wave, together with a receiver for processing the chirped or coded echo signals such that the portion of received signal being detected and integrated from a range zone represents information from a focal point in front of the range zone. Also, continuous rather than pulse operation of the novel reflex-transmission imaging system may be employed by using a continuously variable frequency, or otherwise coded, source and associated receiver. Obviously, a conventional C-scan image may be obtained at the same time a reflex transmission C-scan image is obtained by simply processing those signals reflected from scatterers at the focal point, in a conventional manner, then processing those signals obtained from a range zone opposite the focal point, in the manner of the present invention. It is intended that the above and other such changes and modifications shall fall within the spirit and scope of the invention as defined in the appended claims.

I claim:

1. In an ultrasonic imaging system comprising transducer means for receiving ultrasonic signals reflected from within an object under examination, the combination including
    means for focusing the transducer means at a focal point within the object, and
    means responsive to reflected signals received by the transducer means from a range zone that is opposite the focal point from the transducer means for generating a unitary signal value that is substantially dependent upon, and provides a measure of, attenuation of acoustic waves at the focal point.

2. In an ultrasonic imaging system as defined in claim 1 wherein said transducer means is sharply focused at said focal point while receiving reflected signals from said range zone opposite the focal point.

3. In an ultrasonic imaging system as defined in claim 1 wherein said focusing means includes means for focusing the transducer means at a plurality of focal points at different depths while reflected signals are being received, and
    said means responsive to reflected signals is responsive to signals received by the transducer means from a plurality of range zones each of which is opposite an associated focal point from the transducer means for generating a plurality of unitary signal values substantially dependent upon and providing a measure of attenuation of acoustic waves at the associated focal points.

4. In an ultrasonic imaging system as defined in claim 1 wherein the system is pulse operated.

5. In an ultrasonic imaging system comprising transducer means for receiving ultrasonic signals reflected from within an object under examination, the combination including
    means for focusing the transducer means at a focal point within the object, and
    means responsive to reflected signals received by the transducer means from a range zone that is opposite the focal point from the transducer means for generating a signal related to attenuation of acoustic waves at the focal point, said means for generating a signal related to attenuation of acoustic waves at the focal point including means for detecting the received signal output from the transducer means, and means for integrating the output from said detecting means over a period of time that acoustic waves are received from said range zone.

6. In an ultrasonic imaging system comprising transducer means for receiving ultrasonic signals reflected from within an object under examination, the combination including means for focusing the transducer means at a focal point within the object, said focusing means including means for focusing the transducer means at a plurality of focal points at different depths while reflected signals are being received, means responsive to reflected signals received by the transducer means from a plurality of range zones each of which is opposite an associated focal point from the transducer means for generating a plurality of signals related to attenuation of acoustic waves at the associated focal points, said means for generating a plurality of signals related to attenuation of acoustic waves at the associated focal points including means for detecting the received signal output from the transducer means, and integrating means for integrating the output from the detector means over a plurality of successive time periods that acoustic waves are received from said plurality of range zones.

7. In an ultrasonic imaging system as defined in claim 6 wherein said integrating means includes a plurality of gated integrators which are sequentially operated for sequentially integrating the output from the detector means while acoustic waves are received from said plurality of range zones.

8. In a reflex transmission ultrasonic imaging system for imaging a section within objects such as body parts, said system comprising;

ultrasonic transducer means, transmitter means for energizing the transducer means for beaming ultrasonic energy waves into the object for insonification thereof, said transducer means receiving echo signals from scatterers within the insonified object and converting the same to electrical signals, said transducer means being focused at a focal point within the object, and receiver means responsive to electrical signals from said transducer means for processing signals received from a range zone opposite the focal point from the transducer means so that the processed signals from the range zone provide for a receiver signal output of a level that is a measure of acoustic absorption at the focal point, the amplitude of echo signals from said range zone being significantly dependent upon attenuation at the focal point.

9. In a reflex transmission ultrasonic imaging system as defined in claim 8 including acoustic focusing means for focusing said transducer means.

10. In a reflex transmission ultrasonic imaging system as defined in claim 9 wherein said acoustic focusing means comprises focusing lens means.

11. In a reflex transmission ultrasonic imaging system as defined in claim 8 wherein said ultrasonic transducer means includes an array of transducer elements, and said receiver means includes signal delay means for delaying electrical signals produced by said transducer elements for focusing said transducer means.

12. In a reflex transmission ultrasonic imaging system as defined in claim 11 wherein said signal delay means are variable for focusing at different focal planes within the object.

13. In a reflex transmission ultrasonic imaging system as defined in claim 8 wherein ultrasonic energy waves beamed into the object are focused at the focal point.

14. In a reflex transmission ultrasonic imaging system as defined in claim 13 wherein said transducer means is focused at the focal point when receiving echo signals.

15. In a reflex transmission ultrasonic imaging system as defined in claim 8 wherein said ultrasonic transducer means comprises a unitary transducer which is used both for insonification of the object and reception of echo signals.

16. In a reflex transmission ultrasonic imaging system as defined in claim 8 including beam scanning means for scanning the section to be imaged.

17. In a reflex transmission ultrasonic imaging system as defined in claim 16 wherein the section to be imaged lies in a surface which is substantially normal to the beam axis of the focused transducer means.

18. In a reflex transmission ultrasonic imaging system as defined in claim 17 which includes display means for C-scan display of processed signals, from the receiver means.

19. In a reflex transmission ultrasonic imaging system as defined in claim 16 wherein the section to be imaged lies in a plane which include the beam axis.

20. In a reflex transmission ultrasonic imaging system as defined in claim 19 including display means for B-scan display of processed signals from the receiver means.

21. In a reflex transmission ultrasonic imaging system as defined in claim 20 including scanning means for compound scanning of the transducer means.

22. In a reflex transmission ultrasonic imaging system as defined in claim 8 including beam scanning means for compound scanning the transducer means, said receiver means including means for focusing at different depth focal points, and digital computer means responsive to processed signals for further processing thereof in the preparation of tomographic images.

23. In a reflex transmission ultrasonic imaging system for imaging a section within objects such as body parts, said system comprising;

ultrasonic transducer means, transmitter means for energizing the transducer means for beaming ultrasonic energy waves into the object for insonification thereof, said transducer means receiving echo signals from scatterers within the insonified object and converting the same to electrical signals, said transducer means being focused at a focal point within the object, and receiver means responsive to electrical signals from said transducer means for processing signals received from a range zone opposite the focal point from the transducer means so that the processed signals from the range zone represent information related to attenuation at the focal point, the amplitude of echo signals from said range zone being significantly dependent upon attenuation at the focal point, said receiver means including detector means for detecting received signals, and integrator means for integrating detected signals over the range zone.

24. In a reflex transmission ultrasonic imaging system as defined in claim 23 wherein said integrator means is recurrently operated for recurrently time integrating detected signals, and means for resetting said integrator means after each integrating operation.

25. In a reflex transmission ultrasonic imaging system for imaging a section within objects such as body parts, said system comprising:

ultrasonic transducer means, transmitter means for energizing the transducer means for ultrasonic energy waves into the object for insonification thereof, said transmitter means including means for beaming a series of different-frequency pulses into the object which pulses are focused at different depth focal points, said transducer means receiving echo signals from scatterers within the insonified object and converting the same to electrical signals, said transducer means being focused at said different focal points when receiving echo signals, and receiver means responsive to electrical signals from said transducer means for processing signals received from a range zone opposite the focal point from the transducer means so that processed signals from the range zone represent information related to attenuation at the focal point, the amplitude of echo signals from said range zone being significantly dependent upon attenuation at the focal point, said receiver means comprising a plurality of parallel signal processing channels each of which is responsive to a different one of the different-frequency signals so that a plurality of processed signals from a plurality of range zones opposite the associated focal points are provided which represent information from the different depth focal points.

26. In a reflex transmission ultrasonic imaging system as defined in claim 25 including beam scanning means for obtaining images of a plurality of substantially parallel sections within the object.

27. In a pulsed reflex transmission ultrasonic imaging system for imaging a section within objects, such as body parts, which apparatus includes an ultrasonic transducer and pulse transmitter means for energizing the transducer for beaming ultrasonic energy pulses into the object for pulse insonification thereof, range gated signal processing means responsive to the output from the transducer for processing echo signals received from scatterers over a range zone within the insonified object, and beam focusing means for focusing the transducer at a focal point ahead of the range zone from which echo signals are processed, the amplitude of echo signals from the range zone being substantially dependent upon attenuation at the focal point, said range gated signal processing means having a signal output the level of which provides a measure of attenuation at the focal point.

28. In a pulsed reflex transmission ultrasonic imaging system as defined in claim 27 wherein the transducer is focussed during pulse insonification of the object.

29. In a pulsed reflex transmission ultrasonic imaging system as defined in claim 27 wherein the transducer is focused during operation of the range gated signal processing means.

30. In a pulsed reflex transmission ultrasonic imaging system as defined in claim 27 wherein the transducer is focused both during pulse insonification of the object and during operation of the range gated signal processing means.

31. In a pulsed reflex transmission ultrasonic imaging system as defined in claim 27 wherein the processed signals which result from echo signals which pass through the focal point establish one pixel of a display, said system including beam scanning means for scanning the focal point over the section to be imaged, and means for displaying the processed signals to provide an image of the section at the focal points.

32. In a pulsed reflex transmission ultrasonic imaging system as defined in claim 31 wherein a C-scan display is provided at the display means.

33. In a pulsed reflex transmission ultrasonic imaging system for imaging a section within objects, such as body parts, which apparatus includes an ultrasonic transducer and pulse transmitter means for energizing the transducer for beaming ultrasonic energy pulses into the object for pulse insonification thereof, range gated signal processing means responsive to the output from the transducer for processing echo signals received from scatterers over a range zone within the insonified object, said signal processing means including detector means for detecting received signals, and integrating means for integrating detected signals, and beam focusing means for focusing the transducer at a focal point ahead of the range zone from which echo signals are processed, the amplitude of echo signals from the range zone being substantially dependent upon attentuation at the focal point.

34. In a pulsed reflex transmission ultrasonic imaging system as defined in claim 33 including, means for resetting said integrating means after each range gate operation of the signal processing means.

35. In a reflex transmission ultrasonic imaging method for non-invasive examination of the interior of objects such as body parts from reflections from scatterers within the object of ultrasonic energy, steps including receiving by means of focused transducer means reflected ultrasonic energy and converting the same to electrical signals, detecting electrical signals from the transducer means, integrating detected signals over a time period during which reflected ultrasonic energy is received from a range zone that is opposite the point of focus of the focused transducer means from said transducer means, the integrated signal being related to attenuation at said point of focus, and using the integrated signal to establish one pixel of a display.

36. In a reflex transmission ultrasonic imaging method as defined in claim 35 including scanning the point of focus of the focused transducer means in a surface substantially normal to the acoustic axis thereof for obtaining a C-scan display of pixels.

37. In a reflex transmission ultrasonic imaging method as defined in claim 36 wherein the same transducer means is employed for both transmission and reception of ultrasonic energy pulses, which transducer means is focused at the same focal point during both transmission and reception.

38. In a pulsed reflex transmission ultrasonic imaging method for non-invasive examination of the interior of objects such as body parts, steps comprising pulse insonifying at least a portion of the object with a focused beam of acoustic energy to produce echo signals from scatterers within the object, receiving by focused transducer means echo signals from within the object and converting the same to electrical signals, detecting the electrical signals, and passing the detected signals through integrating means for integrating the same over a time period during which echo signals are received from a range zone opposite the point at which the transducer means is focused from the transducer means whereby the output from the integrating means at the end of the time period is strongly dependent upon attenuation of acoustic waves at the focal point.

39. In a pulsed reflex transmission ultrasonic imaging method as defined in claim 38 wherein the insonifying pulse and focused transducer means are focused at substantially the same focal point.

40. In a pulsed reflex transmission ultrasonic imaging method as defined in claim 38 including, after the end of the time period, supplying the output from the integrating means to display means for visual display thereof.

41. In a pulsed reflex transmission ultrasonic imaging method as defined in claim 40 including resetting the integrating means after the end of the time period, and repeating the claimed steps.

42. A B-scan imaging system comprising transducer means for transmitting ultrasound into an object to be imaged along a beam axis and receiving echo signals reflected from scatterers in said object and generating electrical signals in response thereto, means for focusing said transducer means at focal points at different depths along the beam axis within the object, means responsive to reflected signals received by the transducer means from range zones that are opposite the focal points from the transducer means for obtaining signals related to attenuation of acoustic waves at the focal points, scanning means for compound scanning the beam axis for obtaining signals related to attenuation of acoustic waves at focal points at intersections of intersecting beam axes, and means for generating a B-scan image from said signals related to attenuation of acoustic waves at the focal points, said means for obtaining signals related to attenuation of acoustic waves at the focal points including, (a) means for detecting the electrical signal output from the transducer means, and (b) means for integrating the detected signals over the time periods that acoustic waves are received from said range zones opposite the focal points from the transducer means.

* * * * *